United States Patent [19]

Gilman et al.

[11] Patent Number: 5,579,919

[45] Date of Patent: *Dec. 3, 1996

[54] MEDICAL ELECTRODE PACKAGING TECHNOLOGY

[75] Inventors: Byron L. Gilman, Plymouth; Karl J. F. Kroll, Maple Grove, both of Minn.

[73] Assignee: SurVivaLink Corporation, Minneapolis, Minn.

[*] Notice: The portion of the term of this patent subsequent to Apr. 4, 2012, has been disclaimed.

[21] Appl. No.: 411,102

[22] Filed: Mar. 27, 1995

Related U.S. Application Data

[62] Division of Ser. No. 950,823, Sep. 24, 1992, Pat. No. 5,402,884.

[51] Int. Cl.⁶ ........................................ B65D 73/02
[52] U.S. Cl. ..................... 206/701; 206/727; 206/438
[58] Field of Search ................................ 206/701, 726, 206/727, 728, 210, 438, 363, 460, 461

[56] References Cited

U.S. PATENT DOCUMENTS

| | | | |
|---|---|---|---|
| 3,086,652 | 4/1963 | Lipscomb | 206/328 |
| 3,198,329 | 8/1965 | Golenpaul et al. | 206/65 |
| 3,265,945 | 8/1966 | Jennings et al. | 206/328 |
| 3,585,275 | 6/1971 | Gillemot | 206/328 |
| 3,602,216 | 8/1971 | Moe, Jr. | 128/2.06 |
| 3,685,645 | 8/1972 | Kawaguchi | 206/63.2 |
| 3,701,346 | 10/1972 | Patrick, Jr. et al. | 206/328 |
| 3,830,229 | 8/1974 | Johnson | 206/328 |
| 3,961,623 | 6/1976 | Milani et al. | 128/2.06 |
| 4,029,086 | 6/1977 | Corasanti | 128/2.06 E |
| 4,034,854 | 7/1977 | Beuilacqua | 206/210 |
| 4,423,732 | 1/1984 | Tarjan et al. | 206/438 |
| 4,439,810 | 3/1984 | Shimada et al. | 206/328 |
| 4,487,313 | 12/1984 | Repik et al. | 206/328 |
| 4,779,630 | 10/1988 | Scharnberg et al. | 128/783 |
| 5,402,884 | 4/1995 | Gilman et al. | 206/438 X |

FOREIGN PATENT DOCUMENTS

2483215  12/1981  France ................................ 206/210

*Primary Examiner*—Ted Kavanaugh
*Attorney, Agent, or Firm*—Patterson & Keough

[57] ABSTRACT

The invention provides a sealed package system for housing at least one medical electrode apparatus and for enabling the periodic testing thereof, comprising a thin, generally flat flexible envelope constructed and arranged to form an interior cavity for enclosing a conductive gel contact surface of an electrode apparatus, the envelope having at least one continuous layer of a homogeneous, non-conductive, polymeric material, the envelope further having first and second sides; and a structure for conducting current across the envelope to the interior cavity, the conductive structure being electrically connectible to the electrode conductive contact surface.

19 Claims, 4 Drawing Sheets

MEDICAL ELECTRODE PACKAGING TECHNOLOGY

This application is a division of application No. 07/950,823, filed Sep. 24, 1992, now U.S. Pat. No. 5,402,884.

BACKGROUND OF THE INVENTION

This invention relates to electro-medical apparatus and methods and particularly to packaging structures for medical electrode apparatus. The packaging structures are particularly useful for housing medical electrodes prior to use. And, the packaging structures have features that will allow the stored medical electrodes to be periodically tested during storage.

In the past, various electrode devices and/or methods, including packaging schemes have been used and proposed. However, these devices are generally complex, inefficient to use and have significant shortcomings. Specifically, most electrodes and packaging structures therefor, do not provide the ability to test for readiness after, typically, long periods of storage without compromising the sterility and performance of the electrode.

Despite the need for an electrode device, and packaging therefor, in the art which overcomes the limitations and problems of the prior art, none insofar as is known has been proposed or developed. Accordingly, it is an object of the present invention to provide an electrode system which is relatively simple to manufacture and to use, which is effective at delivering high currents and voltages for use in cardiac defibrillation, which is stable and has a long shelf life, and which permits periodic testing of electrode viability and/or functionality without degrading electrode quality.

SUMMARY OF THE INVENTION

The present invention provides a prepackaged electrode system, comprising:

a. at least one electrode, comprising:
   i) a thin non-conductive base layer having first and second sides;
   ii) a first conductive layer disposed on the first side of the base layer and having connection means associated therewith; and
   iii) a second conductive layer for contact with a patient disposed on the first side of the base layer and in contact with the first conductive layer; and b. a sealed electrode package, comprising:
   i) a flexible envelope constructed and arranged to form an interior cavity for enclosing the second conductive layer of the electrode, the envelope having at least one continuous layer of a non-conductive material; and
   ii) means to conduct current across the envelope to the interior cavity, the means to conduct being electrically connectible to the electrode second conductive layer.

In one embodiment of the electrode system, the electrode conductive layer connection means comprises a conductive lead extending from the first conductive layer, wherein the second conductive layer comprises a gel material, and wherein the package envelope further comprises first and second generally flat sides, the means to conduct current comprising first and second structures disposed on the first side of the envelope, whereby a current loop is formable between the first and second package current conduction means structures through the electrode second conductive layer gel.

In another embodiment of the electrode system, the electrode conductive layer connection means comprises a snap-type connector having conductive current dispersement means disposed on the first side of the base layer and conductive connection means disposed on the second side of the base layer, the current dispersement means and the connection means being communicatively connected via an aperture in the base layer, wherein the second conductive layer comprises a gel material, and wherein the package envelope further comprises first and second generally flat sides, the means to conduct current comprising a first structure disposed on the first side of the envelope and a second structure disposed on the second side of the envelope, whereby a current loop is formable between the first and second package current conduction means structures through the electrode second conductive layer gel, the snap-type connector current dispersement means, and the snap-type connection means.

In another embodiment of the electrode system, the first conductive layer comprises first and second members each having a predetermined surface area and being spacially separated a predetermined distance from one another on the base layer first side, each the member having a conductive lead attached thereto, wherein the second conductive layer comprises a gel material, and wherein the package envelope further has first and second generally flat sides, the means to conduct current comprising first and second separate structures disposed on the first side of the envelope, whereby a current loop is formable between the first and second package current conduction means structures through the electrode current conduction means first member, via its respective the lead, the second conductive layer gel, the electrode current conduction means second member, and its respective the lead.

And in another embodiment of the electrode system, the electrode conductive layer connection means comprises a snap-type connector having conductive current dispersement means disposed on the first side of the base layer and conductive connection means disposed on the second side of the base layer, the current dispersement means and the connection means being communicatively connected via an aperture in the base layer, wherein the second conductive layer comprises a gel material, and wherein the package means to conduct current comprises a single structure which is oriented for connection with the second conductive layer gel of the electrode, whereby a current loop is formable between the package means to conduct, the second conductive layer gel, the snap connector current dispersement means, and the snap connector connection means.

In another embodiment of the electrode system, the electrode conductive layer connection means comprises a conductive lead wherein the second conductive layer comprises a gel material, and wherein the package envelope further comprises first and second generally flat sides, the means to conduct current comprising a conductive strip disposed on the interior of the envelope and extending through the layer periphery joinder area, whereby a current loop is formable between the conductive strip the electrode second conductive layer gel, and the conductive lead.

In another embodiment of the electrode system, the electrode conductive layer connection means comprises a snap-type connector having conductive current dispersement means disposed on the first side of the base layer and conductive connection means disposed on the second side of the base layer, the current dispersement means and the connection means being communicatively connected via an aperture in the base layer, wherein the second conductive layer comprises a gel material, and wherein the package means to conduct current comprises a conductive strip which is connected with the second conductive layer gel of the electrode, whereby a current loop is formable between the conductive strip, the second conductive layer gel, the snap connector current dispersement means, and the snap connector connection means.

In another embodiment of the electrode system, there are two electrodes, each the electrode conductive layer connection means comprising a conductive lead and each the second conductive layer comprising a gel material, the electrode system further comprising a conductive/resistive separator disposed between the second conductive gel layers of the respective electrodes, and wherein the package means to conduct comprises conductive lead means connected to the conductive separator, whereby a current loop is formable between the electrode lead and the package lead means.

These and other benefits of this invention will become clear from the following description by reference to the drawings.

DESCRIPTION OF THE PREFERRED EMBODIMENT

The present invention provides an electrode system for use in the medical arts, particularly in cardiac defibrillation. The system includes cooperating electrode embodiments, packaging embodiments and test instrumentation. The system provides convenient, secure and sterile storage means for electrodes which are easy to manufacture and use. The system also provides a means of periodically testing the operability of the stored electrodes without destroying the packaging or electrodes, and without compromising the sterility of the materials. The teachings of this invention are applicable to electrodes used for either or both transmitting or receiving, although they are particularly beneficial for use in electrodes used in cardiac defibrillation, which electrodes require transfer of particularly high currents and voltages and a high confidence lead in readiness.

Figure 1:
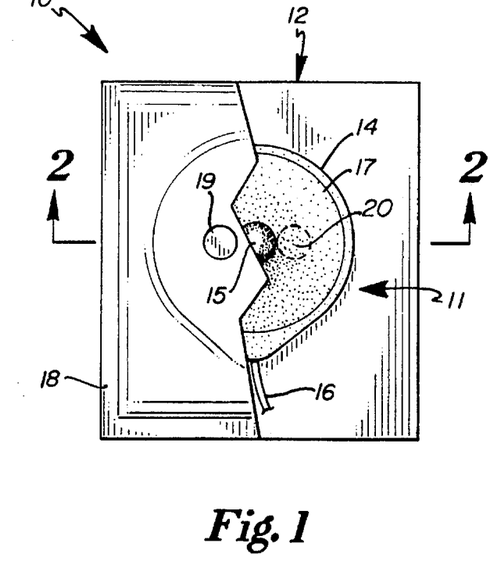
FIG. 1 is a top view of one embodiment of the medical electrode system of the present invention.
Figure 2:
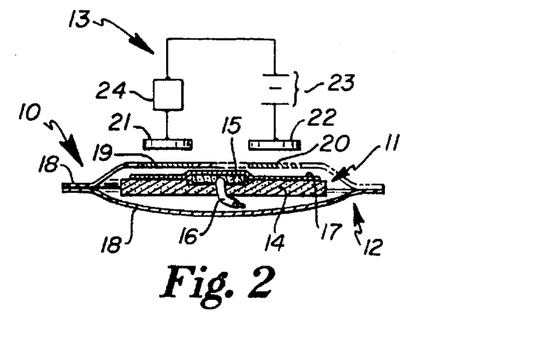
FIG. 2 is a side view, partially in crossection, of the electrode of FIG. 1, and further showing a test apparatus therefor.

Referring to FIGS. 1 and 2 an embodiment of the packaged electrode system 10 is shown to comprise an electrode 11 and a package or enclosure 12. Also shown in FIG. 2 is a test apparatus 13. The electrode 11 is shown to comprise a non-conductive base or backing layer 14, a conductor or conductive layer 15, a lead 16, and a conductive contact layer 17. The base layer 14 is preferably constructed of a thin, flexible polymeric substance such as a urethane foam, or a polyester or polyolefin laminate which provides structural base and insulative properties. Although the base layer 14 is shown to have a surface area which is substantially coextensive with the surface of the contact layer 17, it alternatively may be slightly larger. In such larger configurations, the base layer 14 may have a pressure sensitive adhesive disposed on its patient contact side for increased adhesion to the patient body.

The conductive layer 15 is shown to be disposed on the first or patient side of base layer 14. It functions to transfer (disperse) current or voltage from the lead 16 (or to the lead in a sensing application) to the patient contact layer 17. Although the conductive layer 15 is shown to have a surface area which is smaller than that of the base layer 14 or contact layer 17, it may alternatively have a dimension which is larger than that shown, or even one which is coextensive with the base and contact layers 14 and 17. The conductive layer 15 is preferably a homogeneous, solid, thinly deposited metallic substance, or a conductive ink material. Alternatively, the conductive layer 15 may be formed of a flexible mesh material, a conductive adhesive or a deposited ink pattern. Flexible conductive ink compounds known in the art have a conductive filler of Gold, Silver, Aluminum or other conductive materials.

The lead 16 is preferably an insulated wire conductor which extends from a mating point with the conductive layer 15, through the base layer 14, and then has a freely movable end. Various alternatives of this lead 16 design exist and are useable consistent with the general teachings of the invention, including but not limited to uninsulated wire conductors and conductive strips or traces deposited between the contact layer 17 and the base 14 or conductive layers 15. Such a trace or strip may also extend just beyond the base layer 14 for connection with an ancillary connection means such as a wiring harness including conductive clip means.

The conductive contact layer 17 is preferably a thin layer of semi-liquid gel material. The gel maintains direct electrical contact with the skin, to reduce variations in conductance, and it permits such contact for long periods of time. The gel is a conductive, gelatinous compound which is also flexible for contoured adhesion to the body of a patient. The gel also preferably has a pressure sensitive, moisture resistant adhesive property. Compounds having these characteristics have been developed by Minnesota Mining and Manufacturing, Medtronic, and Lec Tec (Synkara TM), Corporations, all of Minnesota, U.S.A. Generally, these compounds have low resistivities. The contact layer 17 is for direct contact with the patient's body to transfer current or voltage thereto or therefrom. Overall, although the electrode 11 and its constituent elements are shown to have circular configurations, they may alternatively be formed in various other shapes such as rectangular or square patches.

Figure 18:
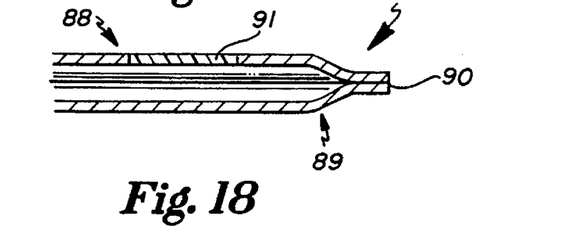
FIG. 18 is a crossectional view of packaging material layers.

The package structure 12 is shown to have an envelope-like structure formed of a substantially continuous thin, homogeneous layer 18 of a polymeric, preferably non-gas permeable, material. Alternatively, as shown in FIG. 18, the package 87 embodiment may have a pouch-like structure formed of a pair of thin, flat homogeneous layers 88 and 89 which are sealed or otherwise merged together at their peripheries or outer edges 90. And, although the package 12 is shown to have a rectangular configuration various other configurations and shapes are also useable consistent with the invention.

Figures 15, 16, 17:
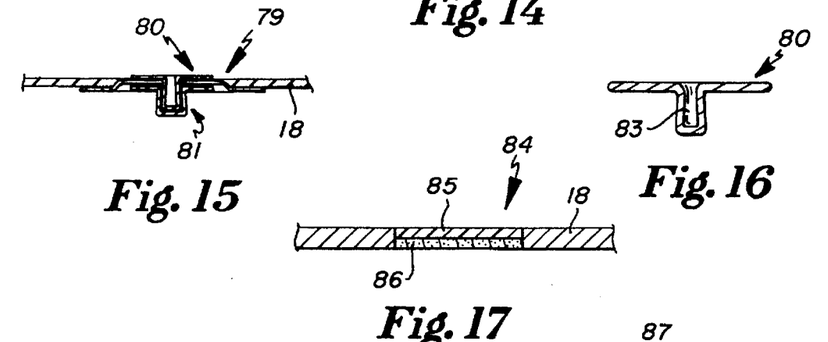
FIG. 15 is a detailed view of a snap-type connection.
FIG. 16 is a detailed view of a top member of the snap connection shown in FIG. 15.
FIG. 17 is a crossectional view of a resistive layer.

The package further comprises a pair of conductive connectors 19 and 20 which are separated a predetermined distance from one another for contact with separate areas of the contact layer 17 of the enclosed electrode 11. The connectors 19 and 20 are conductive areas which are shown to have a unitary construction with the package layer 18. The contacts 19 and 20 may alternatively be formed of thin layer strips of conductive material, or a printed conductive ink, disposed on the interior side of the package layer 18, extending from contact nodes to peripheral contact areas on the exterior of the package 18. Yet another snap-type embodiment 79 is shown in FIGS. 15 and 16 including a connective member 80 disposed on one side of the base layer 18, and a current dispersion member 81 disposed on the opposite side and being connected to the upper member 80 via an aperture in the base 18. The upper member 80 is shown 60 have a base 82 and a mating notch 83 for coupling the lower member 81.

Referring to FIG. 2, the system 10 of the present invention also comprises a test apparatus 13. The test apparatus 13 includes a current source 23, preferably a battery, test circuitry 24, preferably including measurement components and status indication components such as an analog meter, LCD digital display or light emitting diodes, and connectors 21 and 22 for coupling with the package 12 connectors 19 and 20. In use, the test apparatus 13 is connected to the package connectors 19 and 20. The test circuitry 24 is then activated to form a closed current loop to determine whether continuity exists with respect to the enclosed electrode 11, thereby indicating whether the electrode 11 is still functional. Additionally, a load 86 formed of for example a conductive and semi-conductive material layers 85 and 86, may be added to the current loop as for example is shown in FIG. 17, for purposes of measuring the magnitude of current flow for more precise measurement of electrode 11 condition.

In the case of the electrode system embodiment 10, a current loop is formed including the connector 19, the gel of the contact layer 17 (along a substantially horizontal plane), and the connector 20 which is located at a remote location on the contact layer 14 with respect to the connector 19. Current conducts easily in fresh, semi-liquid gel of the contact layer 17. In contrast, no current conducts, or current conduction is attenuated, in stale, dried gel. This is indicative of the need to dispose of the stored electrode without using it. And, this condition is determinable without the need to open the package 12 and thereby risk compromising the freshness or sterility of a viable electrode 11.

Figure 3:
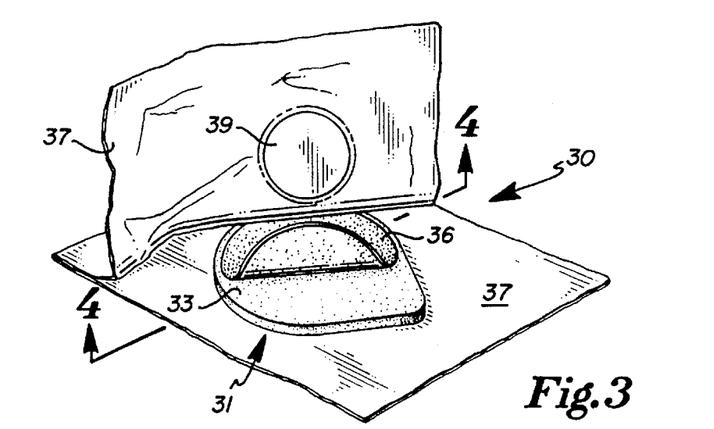
FIG. 3 is a top view of another embodiment of the electrode.
Figure 4:
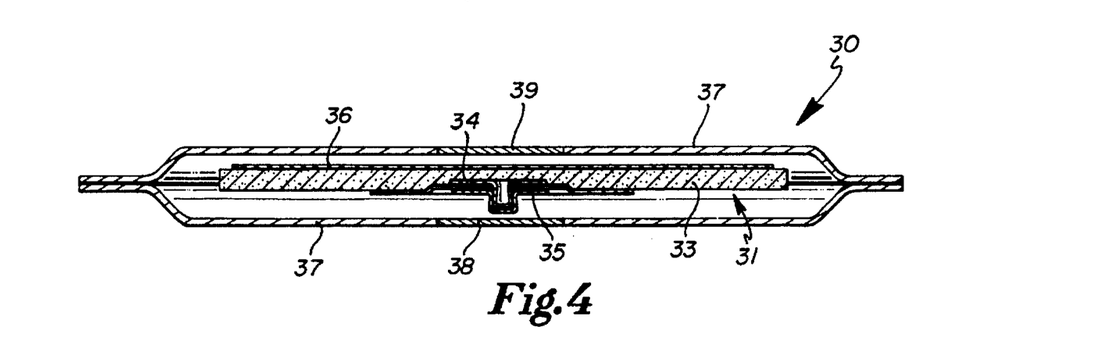
FIG. 4 is a side view of the electrode shown in FIG. 3.

Referring to FIGS. 3 and 4, another embodiment of the packaged electrode system 30 is shown to comprise an electrode 31 and a package or enclosure 32. The electrode 31 is shown to comprise a non-conductive base layer 33, and a conductive gel layer 36. A conductive snap-type connector having a connection member 35 disposed on one side and a current dispersion member 34 disposed on the second side is also shown. The package 32 is shown to have at least one body layer 37 with a pair of contacts 38 and 39 disposed at predetermined locations to electrically connect with the gel layer 36 and contact 35. In a test mode, a current loop is formed between the connector 39, gel layer 36, connector portions 34 and 35 and connector 38.

Figure 5:
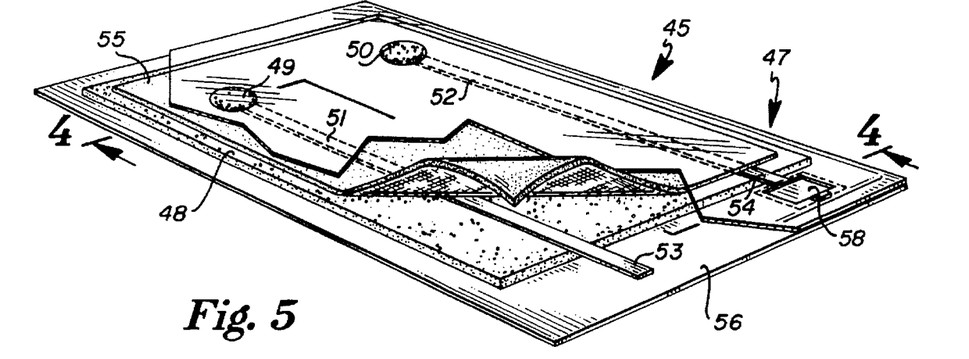
FIG. 5 is a top view of another embodiment of the electrode.
Figure 6:
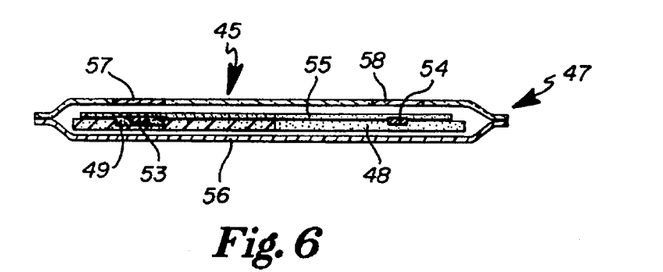
FIG. 6 is a side view of the electrode shown in FIG. 5.

Referring to FIGS. 5 and 6, another embodiment of the packaged electrode system 45 is shown to comprise an electrode 46 and an enclosure 47. The electrode 46 is shown to comprise a non-conductive base layer 48, a conductive gel layer 55, and a pair of separate conductive layers 49 and 50, each of which are shown to have a lead 51 and 52 extending therefrom and terminating in a connective node 53 and 54. The lead pair 51 and 52 (and layer pair 49 and 50) provide a redundant circuit path for increased reliability of use in emergency settings. The package 47 is shown to have at least one body layer 56 with a pair of contacts 57 and 58 disposed at predetermined locations to electrically couple with connective nodes 53 and 54. In a test mode, a current loop is formed between a connector 57 or 58, it's respective connective node 53 or 54 and lead 51 or 52, and its respective conductive layer 49 or 50. In a properly functioning electrode 46, current conducts through the gel 55 from one conductive layer 49 to the other 50, and then back to the test apparatus through the above-mentioned path.

Figure 7:
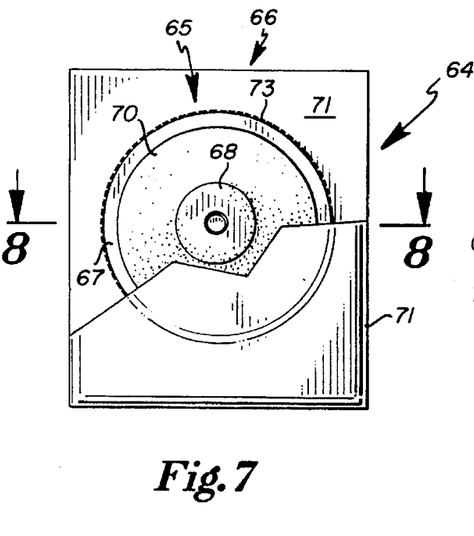
FIG. 7 is a top view of another embodiment of the electrode.
Figure 8:
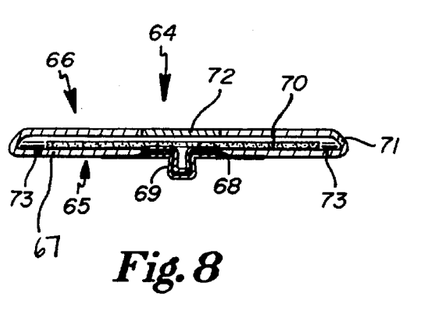
FIG. 8 is a side view of the electrode shown in FIG. 7.

Referring to FIGS. 7 and 8, another embodiment of the packaged electrode system 64 is shown to comprise an electrode 65 and a unitary package 66. The electrode 65 is shown to comprise a non-conductive base layer 67, and a conductive gel layer 70. A snap-type connector with members 68 and 69 electrically couples the gel layer 70.

The package 66 is shown to have at least one body layer 71 which is coupled to the electrode 65 base layer 67 at tear-away perforated lines 73. A connector 72 is shown disposed for contact with the electrode 65 gel layer 70. In a test mode, a current loop is formed between the connector 72, the gel layer 70, and the connector members 68 and 69.

Figure 9:
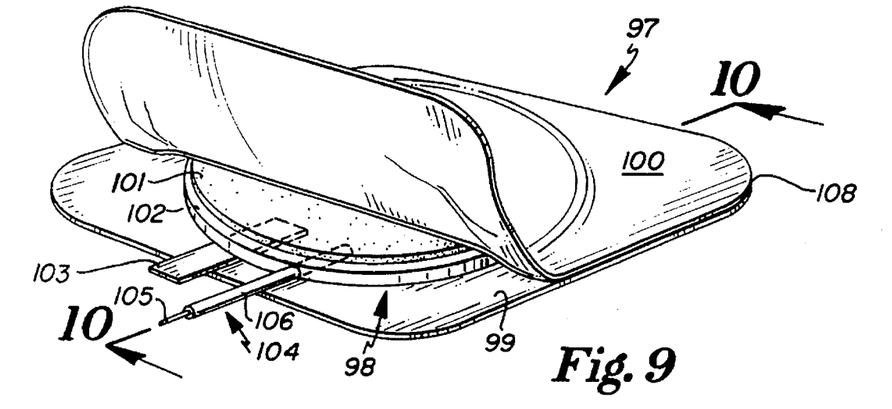
FIG. 9 is a top view of another embodiment of the electrode.
Figure 10:
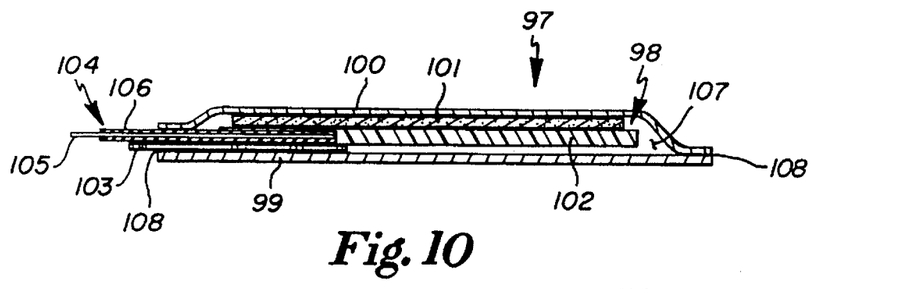
FIG. 10 is a side view of the electrode shown in FIG. 9.

Referring to FIGS. 9 and 10, another embodiment of the packaged electrode system 97 is shown to comprise an electrode 98 and a package. The electrode 98 is shown to comprise a non-conductive base layer 101, a conductive gel layer 102, and a lead 104 having a conductor 105 and an insulator 106, which is shown to be embedded directly in the gel layer 102. Alternatively, the lead may be connected to a conductive current dispersion layer (not shown). A conductive test strip 103 is also shown to be adhered to the surface of the gel 102 at a location remote from the lead 104 for test purposes, and which is designed to release from the gel 102 upon removal of the package layer 99.

The package is shown to have a pair of layers 99 and 100 which overlap to form an interior cavity 107 and are sealingly connected at their peripheries 108. In a test mode, a current loop is formed between the lead 104, the gel layer 102 and the test strip 103, which like the lead 104 is shown extended through the package periphery 108 for contact with an external test apparatus.

Figure 11:
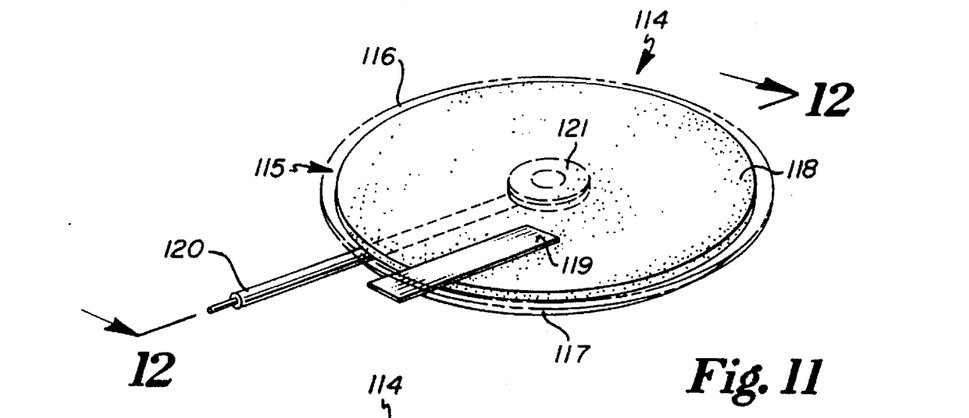
FIG. 11 is a top view of another embodiment of the electrode.
Figure 12:
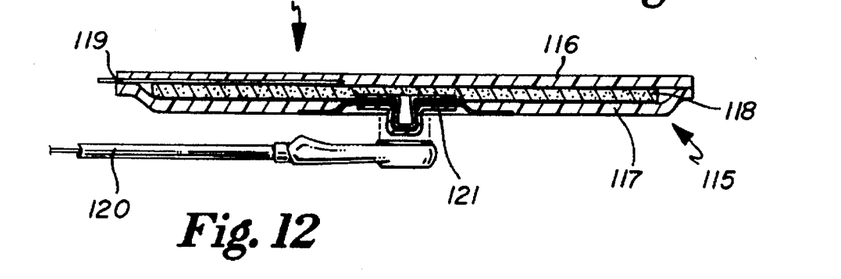
FIG. 12 is a side view of the electrode shown in FIG. 11.

Referring to FIGS. 11 and 12, another embodiment of the packaged electrode system 114 is shown to comprise an electrode 115 and an enclosure. The electrode 115 is shown to comprise a non-conductive base layer 117, and a conductive adhesive gel layer 118 which is connected to a snap-type connection node 121 or the like, and an associated lead 120. The package is shown to comprise a single top layer of non-conductive material 116 which is laminated or adhesively mated to the electrode base layer 117. In use the gel layer 118 is removable from the package layer 116. A test strip 119 is disposed on the interior of the package, adhesively connected to the gel layer 118, and extending to the package exterior. In a test mode, a current loop is formed between the lead 120, node 121, gel layer 118 and the test strip 119.

Figure 13:
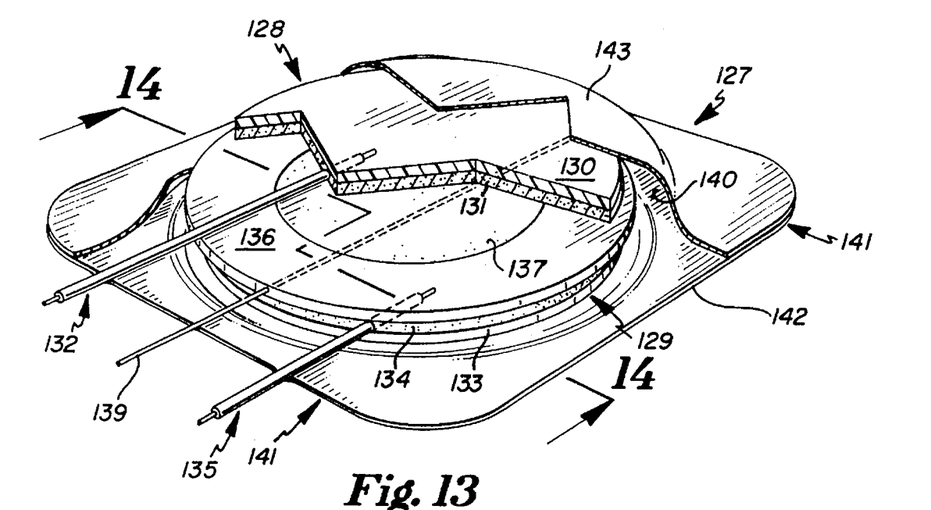
FIG. 13 is a top view of another embodiment of the electrode.
Figure 14:
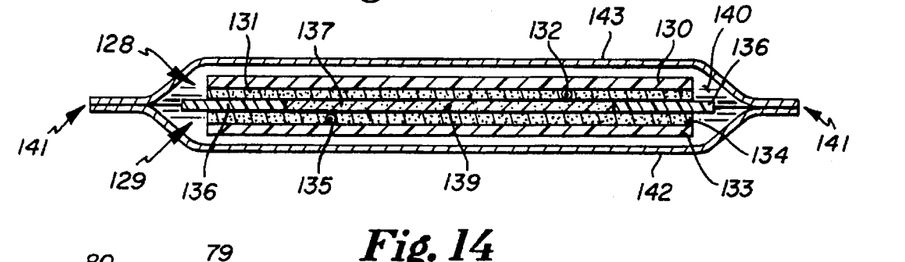
FIG. 14 is a side view of the electrode shown in FIG. 13.

Referring to FIGS. 13 and 14, another embodiment of the packaged electrode system 127 is shown to comprise a pair of electrodes 128 and 129 and a package. The electrodes 128 and 129 are shown to comprise non-conductive base layers 130 and 133, and conductive gel layers 131 and 134. Leads 132 and 135 extend from the respective gel layers 131 and 134. The package is shown to have a pair of overlapping layers 142 and 143 which are sealed at their peripheries 141 to form an enclosure 140 housing the electrodes 128 and 129. Importantly, the electrodes 128 and 129 are oriented with their respective gel layers 131 and 134 mating with a resistive layer 137 (and an optional separator layer 136) formed of a conductive/resistive material as known in the art. A conductive lead 139 or strip extends from the resistive layer through the package periphery 141, as do the electrode leads 132 and 135.

In a test mode, a current loop is formed between, for example, a lead 132, a gel layer 131, the resistive layer 137, and the remaining gel layer 134 and lead 135. The circuit can be altered to include the lead 139.

As many changes are possible to the embodiments of this invention utilizing the teachings thereof, the descriptions above, and the accompanying drawings should be interpreted in the illustrative and not the limited sense.

What is claimed is:

1. A packaged disposable defibrillator electrode, including:
    a first disposable defibrillator electrode, comprising:
       a base layer; and
       a patient-engaging conductive gel layer overlaying the base layer;
    a first insulated lead wire having first and second ends, the first end mounted to the first electrode and electrically interconnected to the conductive gel layer, and the second end configured for electrical interconnection to a defibrillator; and
    a generally gas-impermeable package surrounding the first electrode and the first end of the first lead wire to protect the first electrode prior to use, with the first lead wire extending from the package to enable the second end to be interconnected to a defibrillator prior to the opening of the package and use of the first electrode.

2. The packaged disposable defibrillator electrode of claim 1 and further including:
    a second disposable defibrillator electrode, comprising:
       a base layer; and
       a patient-engaging conductive gel layer overlaying the base layer;
    a second insulated lead wire having first and second ends, the first end mounted to the second electrode and electrically interconnected to the conductive gel layer, and the second end configured for electrical interconnection to a defibrillator; and
    the package also surrounds the second electrode and the first end of the second lead wire to protect the second electrode prior to use, with the second lead wire extending from the package to enable the second end to be interconnected to a defibrillator prior to the opening of the package and use of the second electrode.

3. The packaged disposable electrode of claim 2 wherein the conductive gel layers of the first and second electrodes are electrically interconnected to one another within the package to form an electrical circuit between the second ends of the first and second lead wires and enable testing of the electrical characteristics of the first and second electrodes prior to the opening of the package.

4. The packaged disposable electrode of claim 3 wherein:
    the first and second electrodes are positioned within the package with the conductive gel layers oriented toward one another; and
    the invention further includes a separator layer between the conductive gel layers of the electrodes to enable the electrical interconnection of the conductive gel layers.

5. The packaged disposable defibrillator electrode of claim 1 wherein the package includes a pair of generally gas-impermeable layers having outer edges sealed together, with the lead wire extending between the layers.

6. The packaged disposable defibrillator electrode of claim 5 wherein the gas-impermeable layers of the package include polymeric material.

7. The packaged disposable defibrillator electrode of claim 1 wherein the package includes generally gas-impermeable polymeric material.

8. The packaged disposable defibrillator electrode of claim 1 wherein:
    the base layer of the first electrode includes a layer of flexible, nonconductive material; and
    the conductive gel layer includes an adhesive conductive gel layer.

9. The packaged disposable defibrillator electrode of claim 8 wherein the package includes a pair of generally gas-impermeable layers having outer edges sealed together, with the lead wire extending between the layers.

10. The packaged disposable defibrillator electrode of claim 9 wherein the gas-impermeable layers of the package include polymeric material.

11. The packaged disposable defibrillator electrode of claim 8 wherein the package includes generally gas-impermeable polymeric material.

12. A packaged set of disposable defibrillator electrodes, including:
    a pair of disposable defibrillator electrodes, each electrode comprising:
       a flexible, nonconductive base layer;
       a conductive adhesive gel layer overlaying the base layer; and
       an insulated lead wire having first and second ends, the first end fixedly mounted to the electrode and electrically interconnected to the conductive gel layer, and the second end configured for electrical interconnection to a defibrillator;
    a separator layer between the pair of electrodes, wherein the gel layers of the electrodes are adhesively secured to opposite sides of the separator layer; and
    a generally gas-impermeable package surrounding the pair of electrodes, the separator layer and the first ends of the lead wires, to protect the electrodes prior to use, wherein the lead wires extend from the package to enable the second ends to be interconnected to a defibrillator prior to the opening of the package and use of the electrodes.

13. The packaged set of electrodes of claim 12 wherein the package includes a pair of generally gas-impermeable layers having outer edges sealed together, with the lead wires extending between the layers.

14. The packaged set of electrodes of claim 13 wherein the gas-impermeable layers of the package include polymeric material.

15. The packaged set of electrodes of claim 12 wherein the package includes generally gas-impermeable polymeric material.

16. The packaged set of electrodes of claim 12 wherein the separator layer enables the electrical interconnection of the gel layers to form an electrical circuit between the second ends of the lead wires and enable testing of the electrical characteristics of the electrodes prior to the opening of the package.

17. A packaged set of disposable defibrillator electrodes, including:

a pair of disposable defibrillator electrodes, each electrode comprising:
 a flexible, nonconductive base layer;
 a conductive adhesive gel layer overlaying the base layer; and
 an insulated lead wire having first and second ends, the first end fixedly mounted to the electrode and electrically interconnected to the conductive gel layer, and the second end configured for electrical interconnection to a defibrillator;

a separator layer between the pair of electrodes, wherein the gel layers of the electrodes are adhesively secured to opposite sides of the separator layer and the separator layer enables the electrical interconnection of the gel layers to form an electrical circuit between the second ends of the lead wires and enable testing of the electrical characteristics of the electrodes prior to the opening of the package; and a generally gas-impermeable package surrounding the pair of electrodes, the separator layer and the first ends of the lead wires, to protect the electrodes prior to use, wherein the lead wires extend from the package to enable the second ends to be interconnected to a defibrillator prior to the opening of the package and use of the electrodes.

18. The packaged set of electrodes of claim 17 wherein the package includes a pair of generally gas-impermeable layers having outer edges sealed together, with the lead wires extending between the layers.

19. The packaged set of electrodes of claim 18 wherein the package includes polymeric material.

\* \* \* \* \*

UNITED STATES PATENT AND TRADEMARK OFFICE
CERTIFICATE OF CORRECTION

PATENT NO. : 5,579,919
DATED : December 3, 1996
INVENTOR(S) : Byron L. Gilman, et al.

It is certified that error appears in the above-indentified patent and that said Letters Patent is hereby corrected as shown below:

Col. 5, line 30, delete "60" and insert -- to -- therefore.

Signed and Sealed this

Twenty-second Day of April, 1997

Attest:

BRUCE LEHMAN

Attesting Officer

Commissioner of Patents and Trademarks